United States Patent
Tanaka et al.

(10) Patent No.: US 7,022,346 B2
(45) Date of Patent: Apr. 4, 2006

(54) SPHERICAL POWDER COMPONENTS AND SOLID COSMETIC COMPOSITIONS COMPRISING THEREOF

(75) Inventors: Kojo Tanaka, Morikita-machi (JP); Chie Kawano, Fukuoka (JP)

(73) Assignee: The Procter & Gamble Company, Cincinnati, OH (US)

( * ) Notice: Subject to any disclaimer, the term of this patent is extended or adjusted under 35 U.S.C. 154(b) by 128 days.

(21) Appl. No.: 10/384,274

(22) Filed: Mar. 7, 2003

(65) Prior Publication Data

US 2004/0014841 A1 Jan. 22, 2004

Related U.S. Application Data

(60) Provisional application No. 60/363,626, filed on Mar. 12, 2002.

(51) Int. Cl.
*A61K 9/14* (2006.01)

(52) U.S. Cl. ...................................... 424/489; 424/401

(58) Field of Classification Search ................ 424/401, 424/489
See application file for complete search history.

(56) References Cited

U.S. PATENT DOCUMENTS

| 5,122,418 A | | 6/1992 | Nakane et al. |
| 5,182,103 A | | 1/1993 | Nakane et al. |
| 5,217,327 A | | 6/1993 | Nakanishi |
| 5,234,682 A | * | 8/1993 | Macchio et al. .............. 424/69 |
| 5,382,116 A | | 1/1995 | Nakanishi |

FOREIGN PATENT DOCUMENTS

| JP | 06 271419 | 9/1994 |
| JP | 09100213 | 4/1997 |
| JP | 10338616 | 12/1998 |
| JP | 2000169342 | 6/2000 |

* cited by examiner

*Primary Examiner*—Sreeni Padmanabhan
*Assistant Examiner*—Konata M. George
(74) *Attorney, Agent, or Firm*—Laura L. Whitmer; Vlad Vitenberg

(57) ABSTRACT

Disclosed is a spherical powder component comprising: (1) a large spherical powder having a particle size of from about 10 μm to about 50 μm; and (2) a small spherical powder having a particle size of from about 1 μm to about 10 μm; wherein at least one of the large spherical powder and at least one of the small spherical powder are made of the same material, and the weight ratio of the large spherical powder to the small spherical powder is from about 25:1 to about 1:25.

7 Claims, No Drawings

SPHERICAL POWDER COMPONENTS AND SOLID COSMETIC COMPOSITIONS COMPRISING THEREOF

CROSS-REFERENCE TO RELATED APPLICATIONS

This application claims the benefit of priority to U.S. Provisional Application Ser. No. 60/363,626, filed Mar. 12, 2002, which is herein incorporated by reference.

FIELD OF THE INVENTION

The present invention relates to spherical powder components which contain at least two types of spherical powders having different particle sizes; and solid cosmetic compositions containing such spherical powder components.

BACKGROUND

A foundation composition can be applied to the face and other parts of the body to even skin tone and texture and to hide pores, imperfections, fine lines and the like. A foundation composition is also applied to moisturize the skin, to balance the oil level of the skin, and to provide protection against the adverse effects of sunlight, wind, and other environmental factors.

Foundation compositions in the form of solids, such as loose powders and pressed powders are popular among consumers who enjoy the fresh light feeling on the skin. Solid foundations packaged in compacts are particularly suitable, as such products can be carried for use.

Cosmetic compositions containing spherical powders are known, such as in JPA 60-255712, JPA 9-100213, JPA 10-338616, and JPA 11-209243. While the use of spherical powder enhances smooth spreading of the compositions when applying on the skin, the use generally does not contribute in good adhesion of the composition to the skin. Use of increased amounts of binders may provide improved adhesion, however, may also provide a heavy sticky feeling.

Based on the foregoing, there is a need for a solid cosmetic composition which has balanced benefits in terms of spreadability when applying on the skin, good adhesion on the skin, and fresh light feel on the skin.

None of the existing art provides all of the advantages and benefits of the present invention.

SUMMARY

The present invention is directed to a spherical powder component comprising:
(1) a large spherical powder having a particle size of from about 10 μm to about 50 μm; and
(2) a small spherical powder having a particle size of from about 1 μm to about 10 μm; wherein at least one of the large spherical powder and at least one of the small spherical powder are made of the same material, and the weight ratio of the large spherical powder to the small spherical powder is from about 25:1 to about 1:25.

The present invention is also directed to solid cosmetic composition comprising the spherical powder component.

These and other features, aspects, and advantages of the present invention will become evident to those skilled in the art from a reading of the present disclosure with the appended claims.

DETAILED DESCRIPTION

While the specification concludes with claims particularly pointing out and distinctly claiming the invention, it is believed that the present invention will be better understood from the following description.

All cited references are incorporated herein by reference in their entireties. Citation of any reference is not an admission regarding any determination as to its availability as prior art to the claimed invention.

Herein, "comprising" means that other elements which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

All ingredients such as actives and other ingredients useful herein may be categorized or described by their cosmetic and/or therapeutic benefit or their postulated mode of action. However, it is to be understood that the active and other ingredients useful herein can, in some instances, provide more than one cosmetic and/or therapeutic benefit or operate via more than one mode of action. Therefore, classifications herein are made for the sake of convenience and are not intended to limit an ingredient to the particularly stated application or applications listed.

Spherical Powder Component

The present invention relates to a spherical powder component, and to a cosmetic composition comprising such spherical powder component. The spherical powder component herein is particularly useful for use in solid cosmetic compositions.

The spherical powder component comprises a large spherical powder and a small spherical powder. The large spherical powder has a particle size of from about 10 μm to about 50 μm, preferably from about 10 μm to about 30 μm, more preferably from about 15 μm to about 25 μm; and the small spherical powder has a particle size of from about 1 μm to about 10 μm, preferably from about 3 μm to about 10 μm, more preferably from about 4 μm to about 8 μm. When incorporated in cosmetic compositions, the use of these two different sizes of spherical powder provides balanced benefits in terms of spreadability when applying on the skin, good adhesion on the skin, and fresh light feel on the skin. Without being bound by theory, the large spherical powder is believed to provide good spreadability, while the small spherical powder provides good adhesion. There can be more than one large spherical powder and/or small spherical powder in the spherical powder component. In the present invention, spherical powders having a particle size of less than about 1 μm or greater than about 50 μm are not included in the definition of the large spherical powder or small spherical powder herein. When spherical powders having a particle size of less than about 1 μm are used, they are kept to a level such that it does not impart a gritty feel. When spherical powders having a particle size of over about 50 μm are used, they are kept to a level such that it does not impart an irritating feel. Spherical powders having a particle size of less than about 1 μm or over about 50 μm are preferably not used.

The large spherical powder and the small spherical powder are made of any material that is cosmetically acceptable. At least one of the large spherical powder and at least one of the small spherical powder are made of the same material. Not all of the large and small spherical powders need to be made of the same material. Large and small spherical powders made of different material can be additionally used for implying specific skin benefits such as sebum absorption and pore hiding. Unlimited examples of materials useful for making the large spherical powder and the small spherical powder are; polyacrylates, silicates, sulfates, alumina, metal dioxides, carbonates, celluloses, polyalkylenes, vinyl acetates, polystyrenes, polyamides, acrylic acid ethers, silicones, and mixtures and complexes thereof. Specifically, materials useful herein include polyacrylates such as polymethyl methacrylate and nylon, cross linked polymethyl methacrylate; silicates such as calcium silicate, magnesium silicate, barium silicate, aluminium silicate and silica beads; alumina; metal dioxides such as titanium dioxide and aluminium hydroxide; carbonates such as calcium carbonate, magnesium carbonate; celluloses; polyalkylenes such as polyethylene, and polypropylene; vinyl acetates; polystyrenes; polyamides; acrylic acid ethers such as acrylic acid methyl ether and acrylic acid ethyl ether; polyvinyl pyrrolidones; and silicones such as polyorganosilsesquioxane resin and solid silicone elastomers. Highly preferred materials are polymethyl methacylate.

In one embodiment, polyorganosilsesquioxane resin and solid silicone elastomers may be used for enhancing the effect of hiding skin pores.

Commercially available large and small spherical powders highly useful herein include polymethyl methacylate with tradename GANZ PEARL series available from Ganz Chemical Co., Ltd., and SYLYSIA series available from Fuji Sylysia Chemical, Nylon-12 with tradename NYLON POWDER series available from Toray Dow Corning, vinyl dimethicone/methicone silsesquioxane crosspolymer with tradenames KSP series available from ShinEtsu Chemical Co., Ltd., Tokyo Japan, and hardened polyorgano siloxane elastomers with tradenames TREFIL series available from Toray Dow Corning.

The large spherical powder and the small spherical powder are comprised at a weight ratio of from about 25:1 to about 1:25, preferably from about 20:1 to about 1:20, and more preferably from about 10:1 to about 1:10.

Pigment Component

In one aspect of the present invention, the spherical powder component is incorporated in a solid cosmetic composition comprising a pigment component. In this aspect, the solid cosmetic composition herein comprises from about 75% to about 99%, preferably from about 80% to about 99%, more preferably from about 80% to about 95% of a pigment component, the pigment component comprising from about 2% to about 99%, preferably from about 2% to about 80%, more preferably from about 2% to about 40% of the entire cosmetic composition of the spherical powder component. The pigment component may be made solely of the spherical powder component, or in combination with additional pigments. For providing the particularly preferable powder foundation embodiments of the present invention, additional pigments are typically used. The additional pigments of the pigment component can be treated or untreated, and are selected depending on the desired characteristic of the product, for example, shade, coverage, UV protection benefit, and various skin feel. Herein, powders that do not necessary color the skin are also included in the pigment component.

In one preferred embodiment, the solid cosmetic composition is a powder foundation for the facial skin. In such preferred embodiment, the pigment component further comprises, by weight of the entire composition, from about 1% to about 95% of a base powder other than the large spherical powder or the small spherical powder, from about 2% to about 15% of a titanium dioxide other than the large spherical powder or the small spherical powder; and from about 1% to about 10% of a coloring powder.

The base powders useful herein include clay mineral powders such as talc, mica, sericite, silica, magnesium silicate, synthetic fluorphlogopite, calcium silicate, aluminum silicate, bentonite and montomorilonite. The coloring powders useful herein include pearl pigments such as alumina, barium sulfate, calcium secondary phosphate, calcium carbonate, zirconium oxide, zinc oxide, hydroxy apatite, iron oxide, iron titate, ultramarine blue, Prussian blue, chromium oxide, chromium hydroxide, cobalt oxide, cobalt titanate, titanium oxide coated mica; organic powders such as polyester, polyethylene, polystyrene, methyl metharylate resin, cellulose, 12-nylon, 6-nylon, styrene-acrylic acid copolymers, poly proprylene, vinyl chloride polymer, tetrafluoroethylene polymer, boron nitride, fish scale guanine, laked tar color dyes, and laked natural color dyes. Such base powders, titanium dioxide, and coloring powders may be treated with a hydrophobical treatment agent, including: silicone such as Methicone, Dimethicone and perfluoroalkylsilane; fluorine such as diethanolamine salts of perfluoroalkyl phosphate, fatty material such as stearic acid; metal soap such as aluminium dimyristate; aluminium hydrogenated tallow glutamate, hydrogenated lecithin, lauroyl lysine, aluminium salt of perfluoroalkyl phosphate, and mixtures thereof.

Binder Component

In one aspect of the present invention, the spherical powder component is incorporated in a solid cosmetic composition comprising a binder component. In this aspect, the solid cosmetic composition herein comprises by weight from about 1% to about 25%, preferably from about 2% to about 20%, more preferably from about 2% to about 15% of a binder component. The binder component helps the pigment component from scattering upon use and carriage, and also provides desirable characteristics to the composition. The amount and type of binder component is selected depending on the desired characteristic of the product, for example, product form such as loose powder or compact powder, coverage, adhesion to the skin, and various skin feel. The binder component preferably comprises liquid oils such as silicone oil, and one or both of surfactants and gelling agents.

In one preferred embodiment, the solid cosmetic composition is a powder foundation for the facial skin. In such preferred embodiment, the binder component herein comprises, by weight of the entire composition, from about 1% to about 24% of a silicone oil; and from about 0.01% to about 5% of a gelling agent. In another preferred embodiment of a powder foundation, the binder component herein comprises, by weight of the entire composition, from about 1% to about 24% of a silicone oil; and from about 0.01% to about 5% of a surfactant.

Silicone oils are useful as the binder component herein. Particularly useful are those which have low viscosity but are not too volatile, preferably those having a viscosity of less than about 60 mPas and a volatility as such that not more than 35% of the silicone oil evaporates after standing at 150° C. at normal pressure for 24 hours. Such silicone oils are believed to enhance the fresh and light feel when the composition is applied to the skin.

Silicone oils useful herein also include polyalkyl or polyaryl siloxanes with the following structure (I)

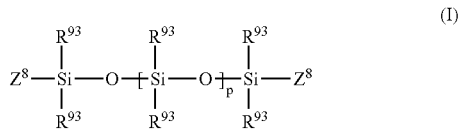

wherein $R^{93}$ is alkyl or aryl, and p is an integer from about 7 to about 100. $Z^8$ represents groups which block the ends of the silicone chains. The alkyl or aryl groups substituted on the siloxane chain ($R^{93}$) or at the ends of the siloxane chains $Z^8$ can have any structure as long as the resulting silicone remains fluid at room temperature, is dispersible, is neither irritating, toxic nor otherwise harmful when applied to the skin, is compatible with the other components of the composition, and is chemically stable under normal use and storage conditions. Suitable $Z^8$ groups include hydroxy, methyl, methoxy, ethoxy, propoxy, and aryloxy. The two $R^{93}$ groups on the silicon atom may represent the same group or different groups. Preferably, the two $R^{93}$ groups represent the same group. Suitable $R^{93}$ groups include methyl, ethyl, propyl, phenyl, methylphenyl and phenylmethyl. The preferred silicone compounds are polydimethylsiloxane, polydiethylsiloxane, and polymethylphenylsiloxane. Polydimethylsiloxane, which is also known as dimethicone, is especially preferred. The polyalkylsiloxanes that can be used include, for example, polydimethylsiloxanes. Polyalkylaryl siloxane fluids can also be used and include, for example, polymethylphenylsiloxanes.

Commercially available herein include methylphenyl polysiloxane with tradenames KF56 available from ShinEtsu Chemical Co., Ltd., SF 1075 METHYL PHENYL FLUID available from the General Electric Company, 556 COSMETIC GRADE FLUID available from Dow Corning, and polydimethylsiloxane having less than 50 mPas with tradenames SH200 available from Dow Corning and the VISCASIL and SF96 series available from the General Electric Company.

Other liquid oils useful as the binder component herein are various grades of mineral oils. Mineral oils are liquid mixtures of hydrocarbons that are obtained from petroleum. Specific examples of suitable hydrocarbons include paraffin oil, mineral oil, dodecane, isododecane, hexadecane, isohexadecane, eicosene, isoeicosene, tridecane, tetradecane, polybutene, polyisobutene, and mixtures thereof. Still liquid other oils useful as the binder component herein are, for example, tridecyl isononanoate, isostearyl isostearate, isocetyl isosteatrate, isopropyl isostearate, isodecyl isonoanoate, cetyl octanoate, isononyl isononanoate, diiso propyl myristate, isocetyl myristate, isotridecyl myristate, isopropyl myristate, isostearyl palmitate, isocetyl palmitate, isodecyl palmitate, isopropyl palmitate, octyl palmitate, caprylic/capric acid triglyceride, glyceryl tri-2-ethylhexanoate, neopentyl glycol di(2-ethyl hexanoate), diisopropyl dimerate, tocopherol, tocopherol acetate, avocado oil, camellia oil, turtle oil, macadamia nut oil, corn oil, mink oil, olive oil, rapeseed oil, eggyolk oil, sesame oil, persic oil, wheat germ oil, pasanqua oil, castor oil, linseed oil, safflower oil, cotton seed oil, perillic oil, soybean oil, peanut oil, tea seed oil, kaya oil, rice bran oil, china paulownia oil, Japanese paulownia oil, jojoba oil, rice germ oil, glycerol trioctanate, glycerol triisopalmiatate, trimethylolpropane triisostearate, isopropyl myristate, glycerol tri-2-ethylhexanoate, pentaerythritol tetra-2-ethylhexanoate, lanolin, liquid lanolin, liquid paraffin, squalane, vaseline, cholesteryl derivatives such as cholesteryl 12-hydroxystearate, cholesteryl macadamiate, cholesteryl stearate, and mixtures thereof. Commercially available oils include, for example, tridecyl isononanoate with tradename CRODAMOL TN available from Croda, HEXALAN available from Nisshin Seiyu, tocopherol acetates available from Eisai, cholesteryl 12-hydroxystearate with tradename SALACOS HS available from Nisshin Oil Mills, Ltd., and cholesteryl macadamiate with tradename YOFCO MAC available from Nippon Fine Chemical Co., Ltd.

A wide variety of oils having UV protecting benefit are suitable for use herein, including those which are typically called UV protecting agents. Preferred among those UV protecting agents are those selected from 2-ethylhexyl-p-methoxycinnamate (commercially available as PARSOL MCX), butylmethoxydibenzoyl-methane, 2-hydroxy-4-methoxybenzo-phenone, 2-phenylbenzimidazole-5-sulfonic acid, octyldimethyl-p-aminobenzoic acid, octocrylene, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, and those by tradenames EUSOLEX 6300, OCTOCRYLENE, PARSOL 1789. These oils can be selected for providing a desired Sun Protection Factor (SPF). SPF is a commonly used measure of photoprotection of a sunscreen against erythema. See Federal Register, Vol. 43, No. 166, pp. 38206–38269, Aug. 25, 1978.

Surfactants are useful as the binder component herein. The type and amount of surfactant is selected depending on the nature of the remainder of the binder component.

The surfactant can be an ester-type surfactant. Ester-type surfactants useful herein include: sorbitan monoisostearate, sorbitan diisostearate, sorbitan sesquiisostearate, sorbitan monooleate, sorbitan dioleate, sorbitan sesquioleate, glyceryl monoisostearate, glyceryl diisostearate, glyceryl sesquiisostearate, glyceryl monooleate, glyceryl dioleate, glyceryl sesquioleate, diglyceryl diisostearate, diglyceryl dioleate, diglycerin monoisostearyl ether, diglycerin diisostearyl ether, and mixtures thereof.

Commercially available ester-type surfactants are, for example, sorbitan isostearate having a tradename CRILL 6 available from Croda, and sorbitan sesquioleate with tradename ARLACEL 83 available from Kao Atras.

The surfactant can be a silicone-type surfactant. Silicone-type surfactants useful herein are (i), (ii), as shown below, and mixtures thereof.

(i) dimethicone copolyols having the structure:

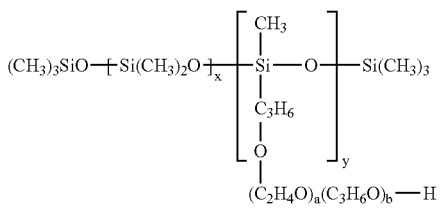

wherein x is an integer from 5 to 100, y is an integer from 1 to 50, a is zero or greater, b is zero or greater, the average sum of a+b being 1-100.

(ii) dimethicone copolyols having the structure:

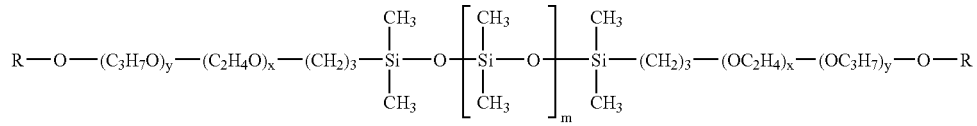

wherein R is selected from the group consisting of hydrogen, methyl, and combinations thereof, m is an integer from 5 to 100, x is independently zero or greater, y is independently zero or greater, the sum of x+y being 1-100.

Commercially available silicone-type surfactants are, for example, DC5225C, BY22-012, BY22-008, SH3746M, SH3771M, SH3772M, SH3773M, SH3775M, SH3748, SH3749, and DC5200, all available from Dow Corning.

Gelling agents are useful as the binder component herein. Gelling agents useful herein include saccharide fatty acid esters, metal soaps, organically modified clay minerals, and mixtures thereof. Particularly useful are those which are thixotropic.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such additional components generally are used individually at levels of no more than about 5% by weight of the composition.

Other components which can be formulated into the compositions of the present invention are; preservatives such as benzyl alcohol, methyl paraben, propyl paraben, sodium dehydro acetate, niacinamide, imidazolidinyl area, and EDTA and its salts, perfumes, ultraviolet and infrared screening and absorbing agents, and others.

Method of Preparation and Method of Use

The spherical power component of the present invention can be used by itself as a loose powder, and can also be suitably incorporated in various cosmetic products such as loose powders, powder foundations, pressed foundations, blushers, eyeshadows, eyebrow cakes, body powders, and other solid forms of cosmetic products. What is meant by "solid" is that the composition is solid and non-flowing at 25° C.

The solid cosmetic composition of the present invention may be made by a method well known in the art. In a suitable process, the solid cosmetic composition is made by the steps of:

1) mixing the pigment component, including the spherical powder component, by a mixer;
2) separately mixing the binder component; and
3) adding the binder component into the pigment component and mixing by a mixer.

Heat may be applied to melt components that are solid at room temperature, or for facilitating homogeneous mixing. When heat is applied, the obtained composition is allowed to cool to room temperature. The obtained composition is placed in a tray container, and pressed as necessary. The tray container is placed in adequate packaging suitable for the user, preferably a compact with a mirror and an applicator for applying the solid composition on the skin.

EXAMPLES

The following examples further describe and demonstrate the preferred embodiments within the scope of the present invention. The examples are given solely for the purpose of illustration, and are not to be construed as limitations of the present invention since many variations thereof are possible without departing from its spirit and scope.

Examples 1–5

The following cosmetic compositions are formed by the process described herein:

| | Compositions | | | | | |
|---|---|---|---|---|---|---|
| NO. | Component | Ex. 1 | Ex. 2 | Ex. 3 | Ex. 4 | Ex. 5 |
| 1 | Polymethyl methacrylate 20 μm*1 | 3 | 1 | 2 | 10 | 20 |
| 2 | Polymethyl methacrylate 8 μm*2 | 8 | 3 | 6 | | |
| 3 | Polymethyl methacrylate 6 μm*3 | | 6 | 12 | 5 | 20 |
| 4 | Nylon-12 5 μm*4 | 2 | | | | |
| 5 | Talc coated with Methicone*5 | 19.59 | 31.1 | 21.1 | 17.6 | 25.1 |
| 6 | Mica coated with Methicone*6 | 15 | | | | 5 |
| 7 | Sericite coated with Methicone*7 | 25 | 35 | 35 | 20 | |
| 8 | Titanium Dioxide coated with Methicone*8 | 10.5 | 12 | 12 | 10 | 5.5 |
| 9 | Mica coated with Titanium Dioxide*9 | | | | 25 | |
| 10 | Methylparaben*10 | 0.3 | 0.3 | 0.3 | 0.3 | 0.3 |
| 11 | Propylparaben*11 | 0.1 | 0.1 | 0.1 | 0.1 | 0.1 |
| 12 | Iron Oxide coated with Methicone*12 | 2 | 2.5 | 2.5 | 2 | 1 |
| 13 | Methylphenyl polysiloxiane*13 | 8.5 | | | | 8.9 |

-continued

| NO. | Component | Ex. 1 | Ex. 2 | Ex. 3 | Ex. 4 | Ex. 5 |
|---|---|---|---|---|---|---|
| 14 | Dimethicone*14 | | 4.8 | 4.0 | 5.9 | 10 |
| 15 | Dextrin palmitate/ethylhexanoate*15 | | 0.1 | 0.5 | 0.1 | 0.1 |
| 16 | Sorbitan monoisostearate*16 | 1 | | | | |
| 17 | D-delta-tocopherol*17 | 0.01 | | | | |
| 18 | Ethylhexyl Methoxy-cinnamate*18 | 5 | 4 | 4 | 4 | 4 |
| 19 | Cholesteryl 12-hydroxy-stearate*19 | | | 0.1 | 0.5 | |

Definitions of Components
*1Polymethyl methacrylate: GANZ PEARL GM-2000 available from GANZ CHEMICAL CO., LTD.
*2Polymethyl methacrylate: GANZ PEARL GM-0800S available from GANZ CHEMICAL CO., LTD.
*3Polymethyl methacrylate: GANZ PEARL GM-0600 available from GANZ CHEMICAL CO., LTD.
*4Nylon-12: NYLON POWDER SP-500 available from TORAY
*5Talc coated with Methicone: SI TALC available from MIYOSHI KASEI, INC.
*6Mica coated with Methicone: SI MICA available from MIYOSHI KASEI, INC.
*7Sericite coated with Methicone: SI SERICITE available from MIYOSHI KASEI, INC.
*8Titanium Dioxide coated with Methicone: SI TITANIUM DIOXIDE IS available from TOSHIKI PIGMENT CO., LTD.
*9Mica coated with Titanium Dioxide: FLAMENCO SUPER PEARL available from THE MEARL
*10Methylparaben: METHYL PARABEN available from UENO PHARMACEUTICALS
*11Propylparaben: PROPYL PARABEN available from UENO PHARMACEUTICALS
*12Iron Oxide coated with Methicone: IRON OXIDE series available from DAITO KASEI KOUGYOU CO., LTD.
*13Methylphenyl polysiloxane: KF56 available from SHINETSU CHEMICAL CO., LTD.
*14Dimethicone: SH200 available from Dow Corning
*15Dextrin palmitate/ethylhexanoate: RHEOPEARL TT available from CHIBA FLOUR MILLING CO., LTD.
*16Sorbitan monoisostearate: CRILL 6 available from CRODA JAPAN KK
*17D-delta-tocopherol: D-DELTA-TOCOPHEROL available from EISAI CO., LTD.
*18Ethylhexyl Methoxycinnamate: PARSOL MCX available from ROCHE VITAMINS JAPAN K.K.
*19Cholesteryl 12-hydroxystearate: SALACOS HS available from Nisshin Oil Mills Method of Preparation The cosmetic compositions of Examples 1–5 are prepared as follows:

Component numbers 1–12 are mixed with a mixer to make a pigment component. Separately, component numbers 17–19 are mixed with the aid of heat, component numbers 15 and 16 are added and mixed until dissolving well, and components 13 and 14 are add and mixed to make a binder component. The binder component is added into the pigment component and mixed by a mixer. The obtained composition is pressed in a tray and set into a compact.

These embodiments represented by the previous examples are useful as solid foundation products. When applied on the facial skin, they provide many advantages. For example, they can provide balanced benefits in terms of spreadability when applying on the skin, good adhesion on the skin, and fresh light feel on the skin.

What is claimed is:

1. A spherical powder component comprising:
   (1) a large spherical powder having a particle size of from about 15 µm to about 50 µm; and
   (2) a small spherical powder having a particle size of from about 1 µm to about 10 µm;

wherein at least one of the large spherical powder and at least one of the small spherical powder are made of the same material, and the weight ratio of the large spherical powder to the small spherical powder is from about 25:1 to about 1:25, and wherein at least one of the large spherical powder and at least one of the small spherical powder are made of polymethyl methacrylate.

2. The spherical powder component of claim 1 wherein the large spherical powder and the small spherical powder are made of material selected from the group consisting of polyacrylates, silicates, sulfates, alumina, metal dioxides, carbonates, celluloses, polyalkylenes, vinyl acetates, polystyrenes, polyamides, acrylic acid ethers, polyvinyl pyrrolidones, silicones, and mixtures and complexes thereof.

3. A solid cosmetic composition comprising by weight:
   (a) from about 75% to about 99% of a pigment component comprising from about 2% to about 99% of the entire cosmetic composition of the spherical powder component of claim 1; and
   (b) from about 1% to about 25% of a binder component.

4. The solid cosmetic composition of claim 3 comprising by weight:
   (a) from about 75% to about 99% of the pigment component comprising by weight of the entire composition:
      (i) from about 2% to about 40% of the spherical powder component
      (ii) from about 1% to about 95% of a base powder other than the large spherical powder or the small spherical powder;
      (iii) from about 2% to about 25% of a titanium dioxide other than the spherical powder, and
      (iv) from about 1% to about 10% of a coloring powder; and
   (b) from about 1% to about 25% of the binder component comprising by weight of the entire composition:
      (v) from about 1% to about 24% of silicone oil; and
      (vi) from about 0.01% to about 5% of a surfactant.

5. The solid cosmetic composition of claim 3 comprising by weight:
   (a) from about 75% to about 99% of the pigment component comprising by weight of the entire composition:
      (i) from about 2% to about 40% of the spherical powder component;
      (ii) from about 1% to about 95% of a base powder other than the large spherical powder or the small spherical powder;
      (iii) from about 2% to about 25% of a titanium dioxide other than the spherical powder; and
      (iv) from about 1% to about 10% of a coloring powder; and
   (b) from about 1% to about 25% of the binder component comprising by weight of the entire composition:
      (v) from about 1% to about 25% of a silicone oil; and
      (vi) from about 0.01% to about 5% of a surfactant.

6. A solid cosmetic composition comprising by weight:
   (a) from about 75% to about 99% of a pigment component comprising from about 2% to about 99% of the entire cosmetic composition of the spherical powder component of claim 2; and
   (b) from about 1% to about 25% of a binder component.

7. A spherical powder component comprising:

(1) a large spherical powder having a particle size of from about 15 μm to about 25 μm; and (2) a small spherical powder having a particle size of from about 1 μm to about 10 μm;

wherein at least one of the large spherical powder and at least one of the small spherical powder are made of polymethyl methacylate, and the weight ratio of the large spherical powder to the small spherical powder is from about 25:1 to about 1:25.

* * * * *